Aug 7, 1951 H. C. SWIM Plant Pat. 1,030
ROSE PLANT
Filed May 5, 1950
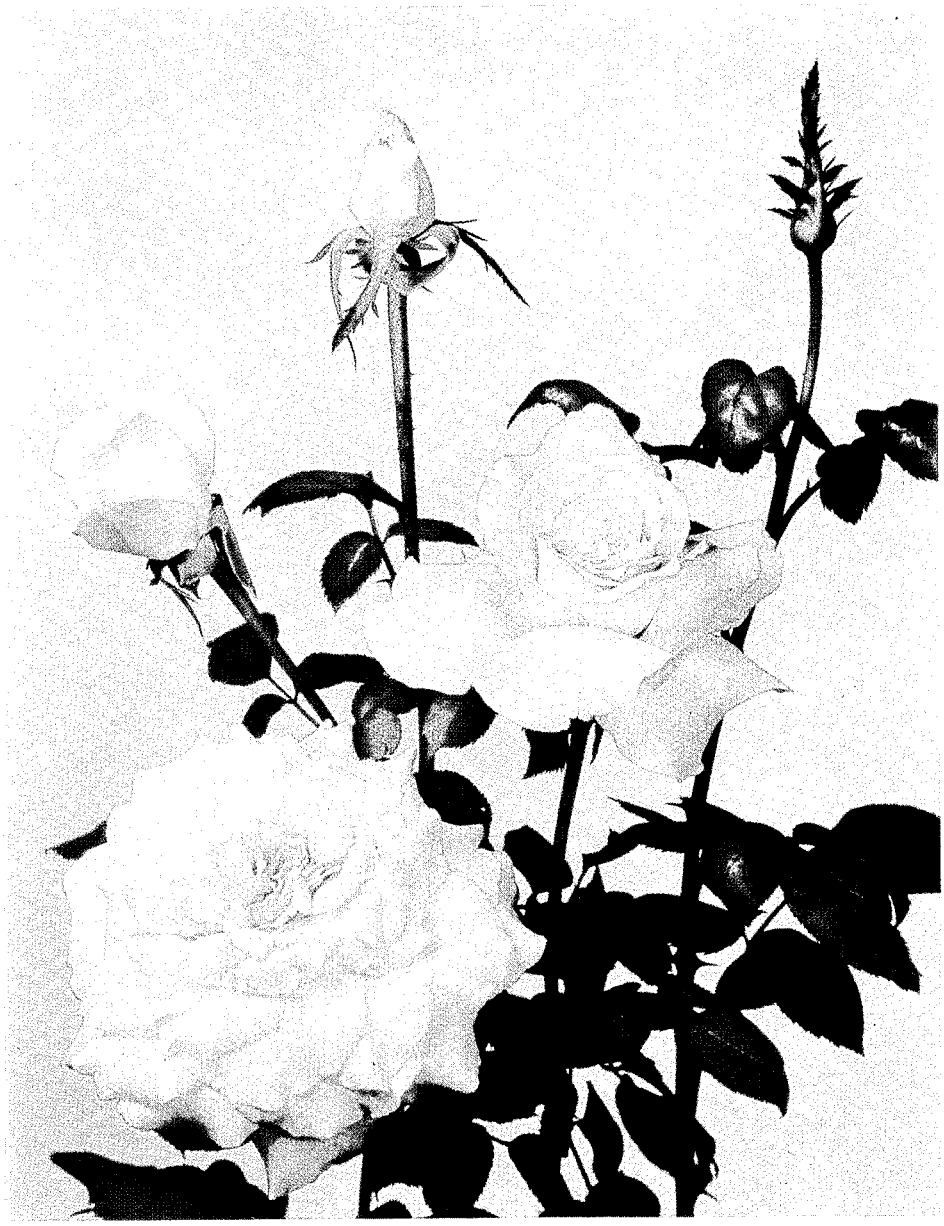
Inventor
H. C. Swim
By: Robert Cook
Attorneys.

Patented Aug. 7, 1951

Plant Pat. 1,030

UNITED STATES PATENT OFFICE 1,030

ROSE PLANT

Herbert C. Swim, Ontario, Calif., assignor to Armstrong Nurseries, Inc., Ontario, Calif., a corporation of California Application May 5, 1950, Serial No. 160,169

1 Claim. (Cl. 47—61)

The present invention relates to a new and distinct variety of rose plant of the hybrid tea class, originated by crossing the popular and well-known variety "Charlotte Armstrong" (Plant Patent No. 455) with the variety "Signora" (Plant Patent No. 201).

This new variety is entirely distinguishable from either of its parents not only as to the coloring of the flowers, but is also dominantly distinct and novel from other hybrid tea rose plant varieties in relation to the following characteristics:

(1) A very vigorous, tall-growing, and free-branching plant producing long stems having few thorns and usually with but a single flower to a stem, which makes this variety desirable not only as a decorative plant for the garden, but for cut flowers as well;

(2) The flowers are produced in abundance and their color ranges in the pastel shades, the central portions of the newly opened flowers being in general tonality darker shades of shrimp red surrounded by pale shades of straw yellow;

(3) In form, the fully opened and very double flower exhibits a regular placement of each petal in an imbricated pattern, giving it a well-balanced appearance.

In comparison with its parents, it is distinct from its seed parent "Charlotte Armstrong" by being more upright in its habit of growth, with glossy foliage as contrasted with the non-glossy foliage of this parent; by having fewer prickles; and by the more numerous petals of its flowers which may be generally described as ranging in color from pale pink to apricot-buff, whereas this parent bears flowers from blood red to cerise in color.

The new variety differs from its pollen parent "Signora" by its production of buds of much greater length than those of this parent, and by a more regular arrangement and more numerous petals of the open flowers whose pale pink to apricot-buff color is quite distinct from the intense scarlet-orange color, shaded with tangerine and cerise which is characteristic of this parent.

Asexual reproduction of this new variety by budding at Ontario, California, shows that the foregoing characteristics come true to form and are established and transmitted through succeeding propagations.

The accompanying drawing illustrates specimens of the new variety, showing the flowers in different stages of development from bud to full-open bloom.

The following is a detailed description of the new variety, with color terminology in accordance with Robert F. Wilson's Horticultural Colour Charts (1941) and Ridgway's Color Standards and Nomenclature (1912):

Type: Tall; bush; outdoor; seedling; for cut flowers and garden decoration.

Class: Hybrid tea.

Breeding: Seedling.

*Seed parent.*—"Charlotte Armstrong" (Plant Patent No. 455).

*Pollen parent.*—"Signora" (Plant Patent No. 201).

Propagation: Holds its distinguishing characteristics through succeeding propagations by budding at Ontario, California.

*Flower*

Locality where grown: Ontario, California.

Flowers borne: Usually singly, rarely two to three to stem; or normal strength, medium to long stems.

Quantity of bloom: Abundant; outdoors.

Continuity: Nearly continuous during growing season.

Fragance: Moderate; tea.

Bud:

*Peduncle.*—Average length to long; heavy; erect; moderately rough; numerous gland-tipped cilia and few prickles. Color—near Cosse Green, Plate V (Ridgway).

*Before calyx breaks.*—Size—medium. Form—medium length; pointed; ovoid; few gland-tipped cilia on the surface of the bud; usually with foliaceous parts extending beyond the tip of the bud equal to one-half of its length.

*As calyx breaks.*—Color—Light Green-Yellow, Plate V (Ridgway).

*Sepals.*—Inner surface with fine, woolly tomentum. The margins have stipitate glands if not covered by adjacent sepals; such glandular margins have several foliaceous appendages on them and toward the sepal tip are serrate. The two margins of a sepal are either both covered or both uncovered, except for the fifth or odd sapal. The glandular-margined sepals have stipitate glands on the outside surface. Non-glandular margins are quite pubescent.

*As first petal opens.*—Size—small. Form—short; conical. Color—Outside: base of Empire Yellow, Plate 603/1, page 66, shading into Straw Yellow Plate 604/2, page 67. In rest of petal margins colored with Azalea Pink, Plate 618/1, page 74; inside— base of Empire Yellow, Plate 603/1, page 66, with rest of petal near Straw Yellow, Plate 604/1, page 67.

*Opening.*—Opens up well. Is not retarded or prevented from opening by cold, hot, wet or dry weather.

Bloom:

*Size when fully open.*—Large; 4 inches to 5 inches.

*Petalage.*—Very double; from 50 to 60 petals, plus 30 to 35 petaloids; arranged regularly.

*Form.*—High centered, becoming flat; petals at first somewhat cupped with tips straight; becoming, later at maturity, somewhat more loosely cupped with tips rolled outward.

Petals:

*Texture.*—Medium thick; moderately soft; with inside slightly satiny and outside slightly shiny.

*Shape.*—Outside—broadly obovate with apex flat. Intermediate—broadly obovate with apex flat. Inside — narrowly obovate. Petaloids in center somewhat irregular in shape.

*Color.*—Colors may be modified by being shaded or tinted with other colors.

This description of a newly opened flower was made from a rose grown outdoors in the month of August, 1949, at Ontario, California:

*Color.*—Outside petal—Outside surface: at base Empire Yellow, Plate 603, page 66, progressively shading to Empire Yellow, Plate 603/2, page 66. Tinted Shrimp Red, Plate 616/1, page 73 toward distal part; inside surface: at base Empire Yellow, Plate 603, page 66, changing soon to Empire Yellow, Plate 603/1, page 66, progressing toward the distal part of petal which is near Chinese Yellow, Plate 606/2, page 68, and 606/3, page 68. *Intermediate petal*—outside surface: base of Empire Yellow, Plate 603, page 66. This changes to Straw Yellow, Plate 604/2, page 67, progressing upward with distal part becoming Shrimp Red, Plate 616/2, page 73; inside surface: base of Empire Yellow, Plate 603, page 66, changing to Empire Yellow, Plate 603/1, and 603/2, page 66, becoming near Straw Yellow, Plate 604/3, page 67, on distal part of petal. *Inner petal*—outside surface: base of Empire Yellow, Plate 603, page 66, shading into Straw Yellow, Plate 604/2, page 67. Further away from base petal strongly shaded with Shrimp Red, Plate 616/2, page 73; inside surface: Empire Yellow, Plate 603/1, page 66, at and near base; toward distal part becoming near Chinese Yellow, Plate 606/2, page 68.

This description was made from a rose that was open for three days outdoors in the month of August, 1949, at Ontario, California:

*Color.*—Outside petal—outside surface: base of Empire Yellow, Plate 603/3, page 66, with rest of petal near cream-white; inside surface: base of Empire Yellow, Plate 603/2, page 66, with rest of petal faded to near cream-white. Inside petal—outside surface: base of Empire Yellow, Plate 603/2, page 66, with rest of petal near cream-white. Occasional petaloid tinted with Shrimp Red, Plate 616/2, page 73; inside surface: base of Empire Yellow, Plate 603/1, page 66, with rest of petal near Straw Yellow, Plate 604/3, page 67.

*General color effect.*—Newly opened flower—center of near Shrimp Red, Plate 616, page 73, surrounded by Straw Yellow, Plate 604/3, page 67. Three days open—between Chinese Yellow, Plate 606/3, page 68, and white.

*Behavior.*—Drop off cleanly except for petaloids which persist; fading to near Baryta Yellow, Plate IV (Ridgway).

*Flower longevity.*—On bush in garden—4 to 5 days in August.

*Reproductive organs*

Stamens: Average number to many; arranged more or less regularly about pistils; a few mixed with petaloids.

Filaments: Medium length to long; most with anthers. Color—Straw Yellow, Plate 604/2, page 67.

Anthers: Flat; large; all open at once approximately. Color—Saffron Yellow, Plate 7/1, page 7, along margins. Middle areas near Lemon Yellow, Plate 4/2, page 4.

Pollen: Sparse. Color—near Saffron Yellow, Plate 7/3, page 7.

Pistils: Average number; approximately 50 in number.

Styles: Uneven; average length; average caliper; somewhat separated. Color—near Cardinal Red, Plate 822/3, page 168.

Stigma: Color—near Mimosa Yellow, Plate 602, page 143.

Ovaries: Most protruding from calyx.

Hips: Average length; globula; smooth; walls thin.

Sepals: Permanent; medium length; straight to recurved; acuminate. Color—inside: near Parrot Green, Plate VI (Ridgway), tinged with Maroon, Plate I (Ridgway). Modified by heavy whitish pubescence; outside: near Parrot Green, Plate VI (Ridgway).

Seeds: Average number; usually small to medium size; 6 to 10 in number.

Foliage:

*Leaves.*—Compound of usually 5 to 7 leaflets; abundant; medium size; moderately thin, somewhat leathery and glossy.

*Leaflets.*—Shape—oval with apex acute to cuspidate. Base — variable. Margin — simply serrate.

*Color.*—*Young*—upper surface—basic color of Lettuce Green, Plate V (Ridgway), shaded with Erythrite Red, Plate 0027, page 190, with a strong band of it around margin; under surface—near Erythrite Red, Plate 0027/2, page 190.

*Rachis.*—Average size. Upper side—grooved with many stipitate glands on edges. Under side—sparsely prickly.

*Stipules.*—Medium length; narrow with moderately short narrow points turning out at an angle of more than 45°.

*Disease.*—Average resistance to mildew.

Growth:

*Habit.*—Bushy; upright; much to moderately branched.

*Growth.*—Very vigorous.

*Canes.*—Medium caliper.

*Main stems.*—Color—near Asphodel Green, Plate XLI (Ridgway); older wood streaked with Cinnamon, Plate XXIX (Ridgway). Large prickles—few to several; short to medium length; hooked slightly downward. Color—varies between Tawny and Russet, Plate XV (Ridgway). Small prickles and hairs—none.

*Branches.* — Color—near Asphodel Green, Plate XLI (Ridgway); if rubbed, color is near Cosse Green, Plate V (Ridgway). Large prickles—few to several; medium length; hooked slightly downward; with medium length elliptical base. Color—clear Dull Green-Yellow, Plate XVII (Ridgway), shaded with Acajou Red, Plate XIII (Ridgway). Small prickles and hairs—none.

*New shoots.* — Color — basically Lettuce Green, Plate 861/3, page 176, tinged with Oxblood Red, Plate 00823/3, page 191. Large prickles—few; medium length; hooked slightly downward; with medium length elliptical base. Color—clear Dull Green-Yellow, Plate XVII (Ridgway), shaded with Acajou Red, Plate XIII (Ridgway). Small prickles and hairs—none.

I claim:

A new and distinct variety of rose plant of the hybrid tea class, characterized as to novelty by its very vigorous, tall-growing and free-branching habits of growth, with long stems having few thorns and usually with but a single flower to a stem, by its abundant production of flowers of colors of general tonality ranging in the pastel shades, with the central portions of the newly opened flowers being darker shades of shrimp red surrounded by pale shades of straw yellow, and by the very double form of the flowers and regular placement of each petal in an imbricated pattern, giving the flowers a well-balanced appearance, substantially as shown and described.

HERBERT C. SWIM.

No references cited.